United States Patent [19]

Hümbert et al.

[11] 4,161,496

[45] Jul. 17, 1979

[54] NOVEL METHOD OF TREATING A CHARGE HYDROCARBON STREAM CONTAINING ISOBUTENE AND ALSO BUTADIENE

[75] Inventors: Heiko Hümbert, Hamburg; Hans-Georg Wegner, Toppenstedt, both of Fed. Rep. of Germany

[73] Assignee: Deutsche Texaco Aktiengesellschaft, Hamburg, Fed. Rep. of Germany

[21] Appl. No.: 873,302

[22] Filed: Jan. 30, 1978

[30] Foreign Application Priority Data

Feb. 16, 1977 [DE] Fed. Rep. of Germany ....... 2706465

[51] Int. Cl.² .............................................. C07C 7/00
[52] U.S. Cl. .................................... 585/836; 585/853; 585/856; 585/864

[58] Field of Search ................... 260/681.5 R, 677 A, 260/677 R

[56] References Cited

U.S. PATENT DOCUMENTS

| 4,031,157 | 7/1977 | Rescalli et al. | 260/681.5 R |
| 4,039,590 | 8/1977 | Ancillotti et al. | 260/681.5 R |

*Primary Examiner*—Veronica O'Keefe
*Attorney, Agent, or Firm*—Thomas H. Whaley; Carl G. Ries; Carl G. Seutter

[57] ABSTRACT

Isobutene is separated from a charge hydrocarbon stream, which may contain butadiene, in two stages in the first of which isobutene is present in excess and in the second of which isobutene is present in deficiency. In the first stage, a strongly acidic ion exchanger is used and in the second stage, an exchanger with a less powerful H+ loading is used.

12 Claims, 1 Drawing Figure

M = METHANOL
E = METHYL TERTIARY BUTYL ETHER
iB = ISOBUTENE
HC = OTHER HYDROCARBONS

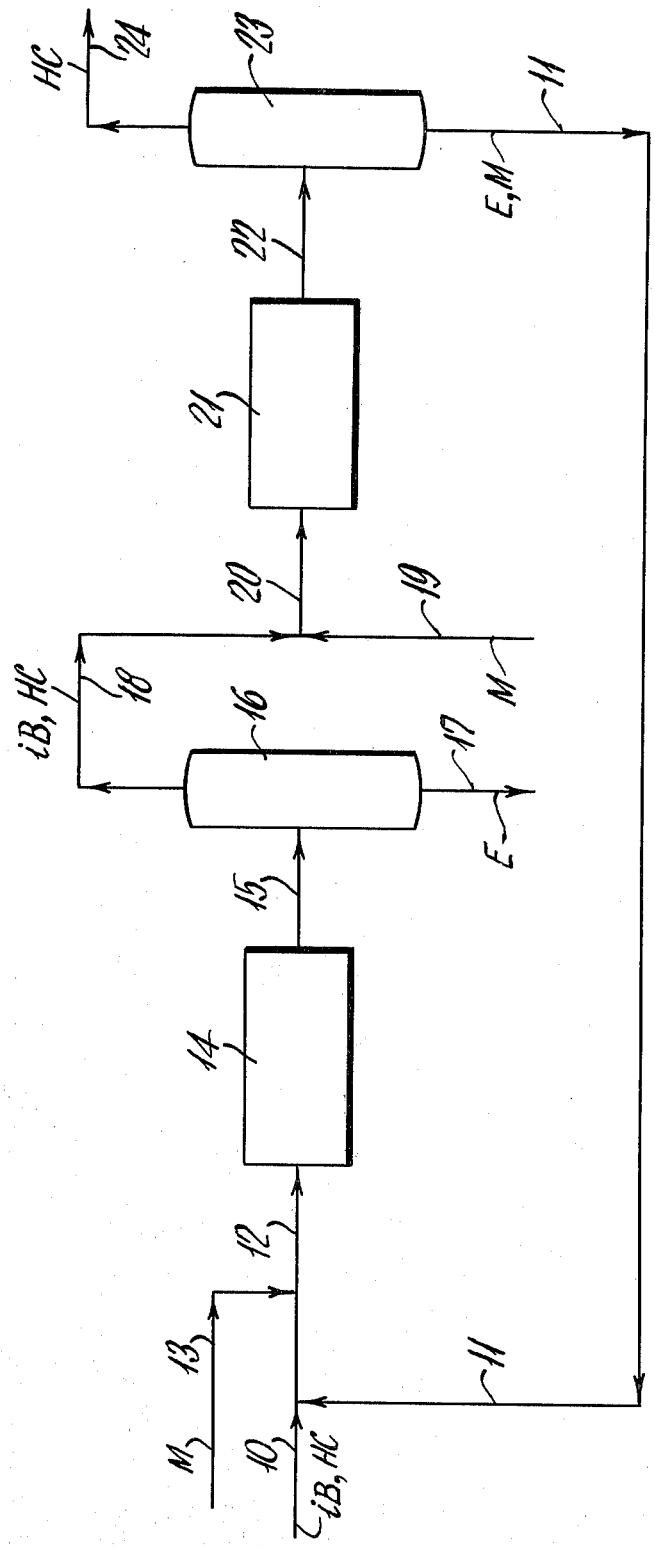

NOVEL METHOD OF TREATING A CHARGE HYDROCARBON STREAM CONTAINING ISOBUTENE AND ALSO BUTADIENE

FIELD OF THE INVENTION

This invention relates to the separation of isobutene from $C_4$ refinery streams.

BACKGROUND OF THE INVENTION

The $C_4$ hydrocarbon fraction which is obtained by the thermal or catalytic cracking of mineral oils is of particular commercial interest because it contains valuable raw materials. Depending on the intensity of cracking especially thermal cracking, the $C_4$ streams contain different quantities of butadiene, n-butylenes, isobutylene, acetylene compounds and saturated hydrocarbons. Inter alia butadiene is the starting product for the production of synthetic rubber and a large group of thermoplastic materials. n-butenes are the starting products for many commercially significant syntheses, for example for synthesizing secondary butanol, methylethylketone and butadiene. The $C_4$ streams are also the feedstock for alkylation plants in which they are converted into anti-knock fuels.

In order to efficiently carry out each of the above-mentioned further processes, it is necessary that the isobutene be removed quantitatively as far as possible. None of the known methods achieves such an extensive removal of isobutylene in the presence of butadiene. Isobutene can be separated from butadiene-free, $C_4$ streams down to approximately 0.3% but this involves the loss, as by isomerization, of substantial quantities of n-butylenes.

A conventional method for the removal of isobutene from $C_4$ streams is the etherification of this hydrocarbon with an alkanol containing 1-4 C-atoms in the presence of an acid ion exchanger as catalyst, because this reaction is selective for olefins with a tertiary C-atom adjacent to the double bond. Methanol is advantageously used as alkanol, since the methyl, tert-butyl ether formed therefrom is a valuable additive for producing anti-knock properties in gasolines.

The reaction of isobutene with a lower alkanol, such as methanol, is an equilibrium reaction. It is known that equilibrium reactions can be shifted to the side of the product if an excess of one of the two reaction partners is used. If isobutene is to be removed from the $C_4$ stream it would therefrom appear to be merely necessary to use an excess of methanol. However, this suffers from the disadvantage that the methyl, tert-butyl ether must be washed for removing the methanol which is a labour-intensive procedure and leads to a loss of ether. A method has therefore been developed in which the quantity of methanol used is equi-molar with the isobutene. The German Offenlegungsschrift No. 25 21 963 can be used as an example. This method operates in two stages in which an excess of isobutene is added in one stage and an excess of methanol is added to the other stage. The reaction is performed with an acid ion exchanger as catalyst. A relatively high flow velocity is required to avoid oligomerization of the isobutene and etherification of the butadiene and similar side reactions. Space velocities of 20 to 50 vol/h are recommended in the above-mentioned German Offenlegungsschrift. Quantitative etherification of the isobutene is of course impossible with such a high flow velocity. If the space velocity is reduced, approximately 3 to 10% of undesirable products will be produced, depending on the butadiene content of the output stream.

OBJECTS OF THE INVENTION

It is an object of this invention to provide a process for treating a charge of hydrocarbon stream containing isobutene to prepare a product hydrocarbon stream containing a substantially lesser quantity of isobutene. Another object of the present invention is to provide a process for treating a charge of hydrocarbon stream containing isobutene and butadiene to prepare a product hydrocarbon stream containing a substantially lesser quantity of isobutene but all of the butadiene. Other objects will be apparent to those skilled in the art.

STATEMENT OF THE INVENTION

In accordance with certain of its aspects, this invention is directed to a method of treating a charge hydrocarbon stream containing isobutene and also butadiene to prepare a product hydrocarbon stream containing a substantially lesser quantity of isobutene but substantially all of the butadiene which comprises;

contacting said charge hydrocarbon stream containing isobutene and butadiene with a deficiency of a lower alkanol in a first reaction zone containing acid ion exchange resin etherification first catalyst thereby forming a first product stream containing the tertiary butyl ether of said lower alkanol plus hydrocarbons and unreacted isobutene;

separating said first product stream, in a first separation zone, into (i) a bottoms containing the tertiary butyl ether of said lower alkanol and (ii) an overhead containing unreacted hydrocarbons, and unreacted isobutene;

contacting said overhead containing said unreacted hydrocarbons and unreacted isobutene with excess lower alkanol, in molar amount greater than the molar amount of unreacted isobutene, in a second reaction zone containing acid ion-exchange resin etherification second catalyst, characterised by a lower hydrogen ion activity than the hydrogen ion activity of said first catalyst, thereby forming a second product stream containing the tertiary butyl ether of said lower alkanol, plus unreacted hydrocarbons including all of the butadiene of the charge hydrocarbon stream and unreacted lower alkanol;

separating said second product stream, in a second separation zone, into (i) a second overhead stream containing unreacted hydrocarbons and unreacted isobutene and (ii) a second bottoms stream containing the tertiary butyl ether of said lower alkanol plus unreacted lower alkanol;

recovering said second overhead hydrocarbon stream containing unreacted hydrocarbons including said butadiene, but practically no isobutene;

recycling said second bottoms stream, containing the tertiary butyl ether of said lower alkanol plus unreacted methanol, to said first reaction zone; and recovering said tertiary butyl ether of said lower alkanol from said bottoms from said first separation zone.

DESCRIPTION OF THE INVENTION

The charge hydrocarbon stream containing isobutene which may be treated by the process of this invention may be a stream containing substantially entirely isobutene in amount approaching 100%. It is however a feature of the process of this invention that, since it may readily be used to separate isobutene from other hydrocarbons, the common charge may contain isobutene together with other hydrocarbons, typically those containing four carbon atoms.

In a typical operation, the charge hydrocarbon may be a $C_4$ stream which is obtained by fractionation of the effluent stream from a thermal or catalytic cracking operation. This stream may commonly contain $C_4$ hydrocarbons and an illustrative stream may contain the following:

| Component | Weight % |
|---|---|
| n-butane | 7.9 |
| iso-butane | 0.8 |
| n-butene-1 | 13.9 |
| cis-butene-2 | 4.5 |
| trans-butene-2 | 5.9 |
| iso-butene | 31.8 |
| 1,3-butadiene | 35.1 |

Although the process of this invention may be used to separate isobutene from streams of saturated hydrocarbons (such as n-butane or iso-butane) which may also contain butenes (which are essentially inactive in the instant process), it is a particular feature of the process of this invention that it possesses outstanding advantages when the charge $C_4$ hydrocarbon stream contains butadiene. Specifically in the process of the instant invention, it is found that it is possible to reduce the isobutene content down to very low levels with no undesirable effects such as isomerization of n-butylenes or oligomerization of butadiene.

In practice of the process of this invention, the charge hydrocarbon stream containing isobutene is passed to a first reaction zone. There is also admitted to the first reaction zone (i) a recycle stream containing desired tertiary butyl ether of lower alkanol plus lower alkanol se and (ii) a charge stream of fresh lower alkanol.

The lower alkanol which may be charged in practice of the process of this invention may include, for example, methyl alcohol, ethyl alcohol, n-propyl alcohol, iso-propanol, or butanol. Preferred of these are the $C_1$–$C_3$ alcohols; and most preferred is methanol.

It is a feature of the charge to the first reaction zone that it contains isobutene plus a deficiency of lower alkanol; i.e. the mole ratio of isobutene to lower alkanol in the first reaction zone is greater than 1. In the preferred embodiment, the mole ratio of isobutene: lower alkanol in the first reaction zone is 1:0.85–0.95, say 1:0.90. It will be apparent that it may be possible to operate with using less than 0.85 moles of lower alkanol per mole of isobutene, but this is much less preferred.

Etherification in the first reaction zone may be preferably carried out in the presence of a solid resin etherification catalyst. These catalysts are acidic ion exchange resins.

The sulfonated resin type catalysts are preferred for use in the present invention. These catalysts include the reaction products of phenol-formaldehyde resins and sulfuric acid ("Amberlite IR-1", "Amberlite IR-100", and "Nalcite MX"). Also useful are the sulfonated resinous polymers of coumarone-indene with cyclopentadiene; sulfonated polymers of coumarone-indene with furfural; sulfonated polymers of coumarone-indene with cyclopentadiene and furfural; and sulfonated polymers of cyclopentadiene with furfural.

The most preferred cationic exchange resins are strongly acidic exchange resins consisting essentially of sulfonated polystyrene resin, for instance, a divinylbenzene cross-linked polystyrene matrix having 0.5–20% and preferably 4–16% of copolymerized divinylbenzene therein, bearing ionizable or functional nuclear sulfonic acid groups. These resins are manufactured and sold commercially under various trade names such as "Dowex 50", "Nalcite HCR" and "Amberlyst 15". As commercially obtained they have a solvent content of about 50% and can be used as is or the solvent can be removed first. The resin particle size may typically be 10 to 50 mesh (U.S. Sieve SUries).

A preferred resin is that available from Dow Chemical Co. under the Dowex-50 trademark having the following characteristics: cross-linking rate of 12%, a particle size of 0.3–1.2 mm, a bulk weight of 870 g/liter, a moist density of 780–820 g/liter, and a dry density of 390–420 g/liter.

In the first reaction zone, which contains the excess of isobutene, it is possible to use acid-form resin i.e. a resin in which all, or substantially all, of the possible acid sites are in fact occupied by hydrogen atoms. Such a resin may be characterized by an activity of greater than 4, and typically 4.2–4.5 mEqH$^+$/g of resin (occasionally referred to in equivalent manner as mValH$^+$/g of resin). The number of acid group equivalents per gram of resin, or more properly the milli-acid equivalents per gram of dry resin may be determined by drying a sample of resin in methanol and thereafter the hexane. The so-dried resin is then titrated with a standard aqueous solution of base e.g. sodium hydroxide.

Although is is possible to use, in the first reaction zone, such an acid resin, it is preferred to use a resin in which at least some, preferably 10–20 atom %, of the acid hydrogen sites on the resin have been deactivated i.e. replaced as by ion-exchange with alkali metal atoms—preferably potassium or more preferably sodium atoms. This first resin catalyst which has thus been deactivated may typically be found to have an activity of 3.3–3.7, preferably 3.4–3.6, say 3.6 milliequivalents of H$^+$ per gram (mEqH$^+$/g) of resin on a dry basis.

Deactivation of the solid resin acid catalyst may be readily effected by placing the resin in a sufficient quantity of distilled water to permit ready stirring of the mix. All of the alkali metal composition, typically potassium chloride or sodium sulfate, is then added at the same time, in amount sufficient to effect the desired degree of deactivation; and the mixture is stirred during addition and thereafter say 2 hours at a rate sufficiently slowly to prevent the exchanger granules from being destroyed.

It is possible to deactivate by use of salts of all monovalent cations which do not form complexes including sodium, potassium, lithium, caesium, etc.; it is preferred to use sodium or potassium. The anion of the salt must of course be one which does not have a detrimental effect on the exchange matrix. Chlorides or sulfates may be particularly suitable.

After the exchange-deactivation is complete, the liquid is drained off and then washed with distilled water. It is thereafter dried by washing with methanol and then freed of methanol by washing with hexane. The degree of deactivation may be determined after drying by washing the exchanger with methanol and h-hexane by titration with aqueous caustic soda.

It is a feature of the process of this invention that the exchange resins may be used indefinitely. Regeneration is not normally required because the H$^+$ activity does not drop during etherification; and the resins are therefore true catalysts. If impurities originating in the starting materials are found to be deposited on the catalyst, they may be removed by flushing with organic solvent.

Etherification in the first reaction zone is effected by reaction of the isobutene and the lower alkanol admitted thereto from (i) the charge hydrocarbon stream, (ii) the charge lower alkanol stream, and (iii) the charge recycle liquor containing lower alkanol and product ether. It is a feature of the process of this invention that in the first reaction zone, in which the mole ratio of isobutene to lower alkanol is 1:4–5, the first ion exchange resin is characterized by an activity of 3.3–3.7 mEq/g which corresponds to that of the fresh resin in which about 10–20 atom % of the acid hydrogen sites have been deactivated by replacement with alkali metal atoms. If the recycle liquor contains the proper amount of lower alkanol, then it is unnecessary to introduce additional lower alkanol.

Etherification is effected in the first reaction zone at about 35° C.–150° C., preferably 50° C.–100° C., say about 90° C. and 50–750 psig, preferably 50–500 psig, say 300 psig. According to the present invention, the space velocity LHSV in the first reaction zone may typically be as low as 4 volumes of charge per volume of catalyst per hour.

In the first reaction zone, isobutylene reacts with lower alkanol, typically methanol, to form the t-butyl ether of the lower alkanol, typically methyl, tertiary-butyl ether. Effluent from the first reaction zone, first product stream, may be passed to a separating operation, typically a flash drum or more preferably a distillation column. Bottoms therefrom contain desired product, the t-butyl ether of the lower alkanol, preferably methyl, t-butyl either. In common operation the yield of e.g. methyl, t-butyl ether (based upon methanol charged to the first reaction zone) may be 92%–95% say about 93%.

Overhead from the first separation zone, containing the unreacted compounds of the charge hydrocarbon stream including isobutene, is withdrawn. Typically this stream contains 0.2%–0.5%, say 0.3% isobutene and substantially all of the butadiene that had been present in the charge hydrocarbon stream, in addition to other $C_4$ hydrocarbons.

In practice of the process of this invention, this overhead stream may be mixed with lower alkanol, preferably methanol, and passed to a second reaction zone. It is a feature of this invention that the charge to the second reaction zone is characterized by the presence of lower alkanol in excess i.e. in molar amount greater than the molar amount of unreacted isobutene in the stream. Although the lower alkanol may be present in amount up to 8 moles per mole of isobutene, more typically the ratio may be up to 4–5, say about 4.

Etherification in the second reaction zone may be effected at substantially the same conditions of pressure and temperature as used in the first reaction zone; the flow rate LHSV may be 0.3–0.7 times that of the first zone, say 0.5; it may be for example 2 vol/vol/hr.

It is a feature of the process of this invention that the second reaction zone contains an acid ion-exchange resin etherification second catalyst characterized by a lower hydrogen ion activity than the hydrogen ion activity of the first catalyst. In a preferred embodiment, the resin catalyst in the second reaction zone is derived from the same resin as that from which the resin catalyst in the first reaction zone is derived—but the second catalyst will be characterized by a lower hydrogen ion activity than that which characterizes the first catalyst.

In one embodiment of the invention, where the first catalyst is characterized by a hydrogen activity of 3.3–3.7 mEq $H^+$/g, preferably 3.4–3.6, say 3.6 mEq $H^+$/g, the second catalyst may be characterized by a hydrogen activity of 1.5–2.5, preferably 2.0–2.2, say 2.1 mEq $H^+$/g. Where the catalysts are derived from the same acid catalyst (e.g. the Dowex 50 brand of polystyrene, cross-linked with divinyl benzene, and sulfonated to contain $—SO_3H$ groups) having an original activity of about 4.2–4.5 mEq $H^+$/g, this may correspond to using a first catalyst in which about 10–20 atom % of the hydrogen acid sites have been replaced by alkali metal (e.g. sodium) and a second catalyst in which about 30–65 atom % of the hydrogen acid sites have been replaced by alkali metal (e.g. sodium).

Effluent, second product stream, from the second reaction zone contains the tertiary butyl ether of the lower alkanol, plus hydrocarbon plus unreacted lower alkanol. This second product stream is passed to a separation operation, typically a flash drum or more preferably a distillation column. Overhead therefrom contains unreacted hydrocarbons, typically containing e.g. n-butane, iso-butane, butenes other than isobutene, and butadiene. It typically contains less than 0.1 wt % isobutene. This stream is recovered.

There is also withdrawn from the second separation operation, second bottoms stream containing tertiary butyl ether of lower alkanol plus unreacted lower alkanol. This stream, which may typically contain 55 w % methyl t-butyl ether and 45w % methanol, is recycled to the first reaction zone.

The invention proposes the use of catalysts more particularly for the second reaction zone in which, due to the severe reduction of the isobutene content resulting from etherification in the first reaction zone, only a small quantity of isobutene is present with a large quantity of butadiene and all reactions of the butadiene, such as etherification crotyl ether and isocrotyl ether are to be avoided. These catalysts are intended to selectively catalyze the etherification of the isobutene so that isobutene can be practically quantitatively removed without creating undesirable side products or causing the loss of valuable butadiene. Furthermore, the invention proposes catalysts which can be adapted to the composition of the $C_4$ streams which are to be treated.

The problem is solved by the use as catalysts of ion exchangers of different hydrogen ion activity. While a commercial, strongly acid exchanger is used in the first reaction zone in which there is a stoichiometric excess of isobutene with respect to alkanol, an exchanger with a less powerful $H^+$ loading is used in the second reaction zone in which there is a stoichiometric excess of the alkanol with respect to the isobutene. This broad embodiment of the invention can be successfully employed if the isobutene from $C_4$ streams always has the same composition and/or it is intended to remove a butadiene content, preferably of less than 30%.

As a rule, however, $C_4$ streams have a varying composition and frequently a very high butadiene content. Allowance must also be made for the fact that the removal of the principal proportion of the isobutene in the first reaction zone enriches the butadiene in the $C_4$ stream, so that the second reaction zone contains mixtures with butadiene contents which are substantially higher than in the first reaction zone. In this instance when the charge stream contains more than about 30 w % butadiene, a highly selective catalyst on which isobutene is exclusively but substantially quantitatively etherified is preferred. According to one preferred embodiment of this aspect of the invention, an ion exchanger deactivated to approximately 3.7–3.3. mEq H+/g is used in the first reaction zone and in the second reaction zone an ion exchanger is used which has been deactivated to 35–70% i.e. 2.5–1.5 mEq H+/g (from the original activity of approximately 4.2–4.5 mEqH+/g).

One special embodiment of the invention is characterized in that an ion exchanger with a hydrogen ion activity of 3.4–3.6 mEqH+/g with an isobutene/methanol mole ratio of 1:0.85–0.95 is used in the first reaction zone for treating a $C_4$ stream containing approximately 35–50% of butadiene and an ion exchanger with a hydrogen ion activity of approximately 2.0–2.2 mEqH+/g with an isobutene/methanol mole ratio of 1:4–5 is used in the second reaction zone.

The catalysts used in accordance with the invention render the process for removing isobutene from $C_4$ streams by means of etherification exceptionally flexible, which is not the case with commercialy available ion exchangers. The process can be adapted to the composition of the $C_4$ starting streams as well as to the relevant purpose of the treated $C_4$ streams by greater or lesser deactivation of the ion exchanger, more particularly that for the second reaction zone. Ion exchangers which have been less intensively deactivated can be used in the second reaction zone if the butadiene content is low or if the streams are free of butadiene. However, a strongly deactivated ion exchanger is used if the butadiene content is high. Surprisingly, it has been found that an ion exchanger with such a low H+ activity as approximately 2 mEqH+/g dry exchanger, selectively etherifies isobutene in the presence of large quantities of butadiene while a non-deactivated ion exchanger would also etherify substantial quantities of butadiene under the same conditions.

All commercially available strongly acid ion exchangers and exchangers with less intensive acid loading can be used as ion exchangers. Macroporous organic exchangers consisting of a matrix of polystyrene, cross-linked with divinylbenzol, and supporting $SO_3H$ groups as ion-forming anchor groups, are particularly preferred. These exchangers are used preferably under water-free conditions. Water is removed by washing the exchanger with methanol and subsequently with n-hexane.

The use according to the invention of ion exchangers of different hydrogen ion activity facilitates a more selective removal than hitherto of isobutene from $C_4$ hydrocarbon streams. The isobutene content can be reduced to 0.2%. It is however also readily feasible to achieve isobutene content values of 200 ppm if the mole ratio of isobutene to methanol is increased to 1:8 in the second reaction zone. Butadiene is etherified or polymerized only to a slight extent owing to the surprisingly high selectivity of the deactivated ion exchanger as regards etherification of isobutene.

DESCRIPTION OF A PREFERRED EMBODIMENT

Practice of the novel process of this invention may be apparent from the following description of a preferred embodiment wherein, as elsewhere in this specification, all parts are parts by weight unless otherwise specifically noted. The accompanying drawing represents schematically a flow sheet of one technique whereby the process of this invention may be carried out. It will be apparent to those skilled in the art that the drawing may show major pieces of equipment, and that various pumps, valves, heat exchangers, collection drums, etc. may not be shown.

In this embodiment of the process of this invention, there is admitted through line 10 a charge hydrocarbon stream having the following composition, showing parts by weight:

| Component | Parts | Wt % |
| --- | --- | --- |
| n-butane | 110.6 | 7.9 |
| iso-butane | 11.2 | 0.8 |
| n-butene-1 | 194.6 | 13.9 |
| cis-butene-2 | 63.0 | 4.5 |
| trans-butene-2 | 82.6 | 5.9 |
| isobutene | 445.2 | 31.8 |
| butadiene-1,3 | 491.4 | 35.1 |
| | 1398.4 | |

Recycle stream is added from line 11 (to line 10) containing 114 parts of methanol and 109 parts of methyl, t-butyl ether. Fresh methanol (127.7 parts) is added through line 13. The stream in line 12 is characterized by a mole ratio of isobutene:methanol of 1:0.9. This stream is admitted to the first reaction zone 14.

The stream in line 12 contains:

| Component | Parts |
| --- | --- |
| isobutene | 445.2 |
| Methanol | 229 |
| methyl, t-butyl ether | 109 |
| $C_4$ hydrocarbons (ex isobutene) | 953 |
| | 1736 |

In reaction zone 14, there is a body of DOWEX-50 brand resin catalyst—a macroporous matrix of polystyrene, cross-linked (12%) with divinyl benzene and bearing —$SO_3H$ groups. The particle size of the resin is 0.3–1.2 mm; and it has a bulk weight of 870 g/l, a moist density of 780–820 g/l, and a dry density of 390–410 g/l. Prior to placement in the reaction zone, the resin is submerged in aqueous sodium chloride for 2 hours with agitation during which time so many hydrogen acid sites are replaced by sodium to yield a resin having a hydrogen ion activity of 3.6 mEqH+/g (based on resin which has been dried with methanol followed by hexane).

Reaction in the first stage 14 occurs at 70° C. and 10 bar and LHSV of 4 to give in line 15 a product stream having the following composition, analyzed by gas chromatography.

| Components | Parts | wt % |
| --- | --- | --- |
| n-butane | 110.6 | 6.4 |
| iso-butane | 11.2 | 0.6 |
| n-butene-1 | 194.6 | 11.2 |
| cis-butene-2 | 63.0 | 3.6 |
| trans-butene-2 | 82.6 | 4.8 |
| isobutene | 70 | 4.0 |
| butadiene-1,3 | 491.4 | 28.3 |
| methanol | 14.8 | 0.9 |
| methyl, t-butyl ether | 697.7 | 40.2 |
| | 1736 | |

This stream is admitted to first separation operation 16, a distillation column, at a flash zone temperature of 80° C. and under elevated pressure. Bottoms recovered in line 17 include 697 parts of methyl, t-butyl ether, a yield of 93.5% based on methanol charged to the reaction zone 14.

Overhead in line 18 contains the following, analyzed by gas chromatography

| Component | Parts |
|---|---|
| isobutene | 70 |
| methanol | 14.8 |
| C$_4$ hydrocarbons (ex isobutene) | 953 |

To this stream there is added through line 19, 138.8 parts of methanol to yield in line 20 a charge stream to second reaction zone having a mole ratio of 1:4.

The catalyst in second reaction zone 21 is, in this embodiment, prepared in the same manner as is the catalyst used in the first reaction zone 14 except that to prepare the second catalyst the fresh charge acid resin has been contacted with aqueous sodium chloride of higher concentration and for a longer time to give product resin wherein the acid hydrogen sites are replaced by sodium atoms to give a resin having an activity of 2.1 mEqH+/g (referred to the dry ion exchanger).

Reaction conditions are the same as in the first reaction zone except that the space velocity LHSV is 2 volumes of fluid per volume of catalyst.

Effluent in line 22 contains the following, analyzed by gas chromatography:

| Component | Parts |
|---|---|
| isobutene | 2.9 |
| methanol | 121.2 |
| methyl, t-butyl ether | 109 |
| C$_4$ hydrocarbons (ex isobutene) | 953 |

The second product stream in line 22 is passed to second separation operation 23, a distillation column, at a flash zone temperature of 80° C. and under elevated pressure. Bottoms recovered in line 17 includes 109 parts of methyl, t-butyl ether and 114 parts of methanol. Overhead recovered in line 24 includes the following, analyzed by gas chromatography:

| Component | wt % |
|---|---|
| isobutene | 0.3 |
| other C$_4$ hydrocarbons | |
| n-butane | 10.9 |
| iso-butane | 1.2 |
| n-butene-1 | 20.0 |
| cis-butene-2 | 6.6 |
| trans-butene-2 | 9.2 |
| butadiene-1,3 | 51.2 |
| methanol | 0.7 |

EXAMPLE II

In this example of the process of this invention, the process was carried out as in Example I. It was found that the composition of the residual gas stream in line 24 was as follows, analyzed by gas chromatography:

| Component | wt % |
|---|---|
| isobutene | 0.1 |
| other C$_4$ hydrocarbons | |
| n-butane | 11.1 |
| iso-butane | 1.0 |
| n-butene-1 | 20.2 |
| cis-butene-2 | 6.7 |
| trans-butene-2 | <0.1 |
| butadiene-1,3 | 51.2 |
| methanol | 0.7 |

From Examples I–II, it is thus apparent that it is possible to reduce the content of isobutene to low levels with little or no decrease in the content of other unsaturates including butadiene.

EXAMPLE III

In this example, the process was carried out under the same conditions and with the system as in Example I. It was found that the composition of the charge stream admitted through line 10 was as follows, analyzed by gas chromatography:

| C$_4$ component | parts | wt % |
|---|---|---|
| n-butane | 59.1 | 4.2 |
| isobutane | 11.3 | 0.8 |
| n-butene-1 | 201.1 | 14.3 |
| cis-butene-2 | 43.6 | 3.1 |
| trans-butene-2 | 60.5 | 4.3 |
| isobutene | 438.8 | 31.2 |
| butadiene-1,3 | 592.1 | 42.1 |

The recycle stream is passed via line 11 to line 10, comprising 80 parts of methanol and 84.3 parts of methyl-tert. butyl ether. 162.5 parts of fresh methanol were added through line 13. The stream in line 12 is characterised by a mole ratio of isobutene to methanol of 1:0.95 and has the following composition:

| Component | parts |
|---|---|
| isobutene | 438.8 |
| methanol | 238.0 |
| methyl-tert.butyl ether | 84.3 |
| C$_4$ hydrocarbons (ex isobutene) | 967.6 |
| | 1728.7 |

The reaction conditions (70° C. and 10 bar) in reactor 14 were the same as in Example I; the liquid hourly space velocity was adjusted to 4 volumes of liquid per volume of catalyst and hour to give in line 15 a product stream having the following composition:

| Component | parts | wt. % |
|---|---|---|
| n-butane | 59.1 | 3.4 |
| isobutane | 11.3 | 0.7 |
| n-butene-1 | 201.1 | 11.6 |
| cis-butene-2 | 43.6 | 2.5 |
| trans-butene-2 | 60.5 | 3.5 |
| isobutene | 54.6 | 3.2 |
| butadiene-1,3 | 292.1 | 34.2 |
| methanol | 18.7 | 1.1 |
| methyl-tert. butyl ether | 678.8 | 39.8 |
| | 1728.8 | |

The stream is admitted via line 15 to separator 16 wherein, subsequent to venting, 687.8 parts of methyl-tert.butyl ether separate out which is equivalent to a yield of 92.2 per cent, based on the methanol charged to reactor 14. The ether is recovered via line 17.

It was found that the composition of the residual gas stream in line 18 was as follows, analyzed by gas chromatography:

| Components | parts |
|---|---|
| isobutene | 54.6 |
| methanol | 18.7 |
| C₄ hydrocarbons (ex isobutene) | 967.6 |

To this stream there is added through line 19, 110 parts of methanol to yield in reactor 21 a charge stream having a mole ratio of isobutene to methanol of 1:4. As in Example 1, the reaction conditions were the same as employed in reactor 14; the liquid hourly space velocity was 2 volumes of liquid per volume of catalyst.

In line 22 the effluent stream from reactor 21 contains the following:

| Component | parts |
|---|---|
| isobutene | 1.0 |
| methanol | 94.2 |
| methyl-tert.butyl ether | 84.3 |
| C₄ hydrocarbons (ex isobutene) | 967.6 |

Subsequent to venting, 84.3 parts of methyl-tert.butyl ether and 80 parts of methanol separate out in separator 23.

The composition of the residual gas stream in line 24 was as follows:

| Component | parts | wt. % |
|---|---|---|
| isobutene | 1.0 | 0.1 |
| other hydrocarbons | | |
| n-butane | 59.1 | 6.0 |
| isobutane | 11.3 | 1.2 |
| n-butene-1 | 201.1 | 20.5 |
| cis-butene-2 | 43.6 | 4.5 |
| trans-butene-2 | 60.5 | 6.1 |
| butadiene-1,3 | 592.0 | 60.2 |
| methanol | 14.0 | 1.4 |

We claim:

1. The method of treating a charge hydrocarbon stream containing isobutene and also butadiene to prepare a product hydrocarbon stream containing a substantially lesser quantity of isobutene but substantially all of the butadiene which comprises contacting said charge hydrocarbon stream containing isobutene with a deficiency of a lower alkanol in a first reaction zone containing acid ion-exchange resin etherification first catalyst thereby forming a first product stream containing the tertiary butyl ether of said lower alkanol plus hydrocarbon and unreacted isobutene;

separating said first product stream, in a first separation zone, into (i) a bottoms containing the tertiary butyl ether of said lower alkanol and (ii) an overhead containing unreacted hydrocarbons and unreacted isobutene;

contacting said overhead containing said unreacted hydrocarbons and unreacted isobutene with excess lower alkanol, in molar amount greater than the molar amount of unreacted isobutene, in a second reaction zone containing acid ion-exchange resin etherification second catalyst, characterized by a lower hydrogen ion activity than the hydrogen ion activity of said first catalyst, thereby forming a second product stream containing the tertiary butyl ether of said lower alkanol, plus unreacted hydrocarbons and unreacted lower alkanol;

separating said second product stream, in a second separation zone, into (i) a second overhead stream containing unreacted hydrocarbons and unreacted isobutene and (ii) a second bottoms stream containing the tertiary butyl ether of said lower alkanol, plus unreacted lower alkanol;

recovering said second overhead stream containing unreacted hydrocarbons and unreacted isobutene;

recycling said second bottoms stream, containing the tertiary butyl ether of said lower alkanol plus unreacted methanol, to said first reaction zone; and recovering said tertiary butyl ether of said lower alkanol from said bottoms from said first separation zone.

2. The method of treating a charge hydrocarbon stream containing isobutene to prepare a product hydrocarbon stream containing a substantially lesser quantity of isobutene as claimed in claim 1 wherein 10–20 atom % of the acid hydrogen sites on the first ion-exchange resin catalyst have been deactivated by replacement with alkali metal ions.

3. The method of treating a charge hydrocarbon stream containing isobutene to prepare a product hydrocarbon stream containing a substantially lesser quantity of isobutene as claimed in claim 1 wherein said first ion-exchange resin is characterized by an activity of 3.3–3.7 mEqH+/gram.

4. The method of treating a charge hydrocarbon stream containing isobutene to prepare a product hydrocarbon stream containing a substantially lesser quantity of isobutene as claimed in claim 1 wherein 30–65 atom % of the acid hydrogen sites on the second ion-exchange resin catalyst have been deactivated by replacement with alkali metal atoms.

5. The method of treating a charge hydrocarbon stream containing isobutene to prepare a product hydrocarbon stream containing a substantially lesser quantity of isobutene as claimed in claim 1 wherein said first ion-exchange resin catalyst is characterized by an activity of 1.5–2.5 mEqH+/gram.

6. The method of treating a charge hydrocarbon stream containing isobutene to prepare a product hydrocarbon stream containing a substantially lesser quantity of isobutene as claimed in claim 1 wherein at least one of said first and said second ion-exchange resin catalysts is a polystyrene resin, cross-linked with divinyl benzene, which resin has been sulfonated to contain —SO₃H groups, said resin having been deactivated by replacement of at least a portion of the acid hydrogen sites with alkali metal atoms, said resin having, prior to deactivation an activity of about 4.2–4.5 mEqH+/g of resin.

7. The method of treating a charge hydrocarbon stream containing isobutene to prepare a product hydrocarbon stream containing a substantially lesser quantity of isobutene as claimed in claim 1 wherein at least one of said first and second resin catalysts is a sulfonated coal which has been deactivated by replacement of at least a portion of the acid hydrogen sites with alkali metal atoms.

8. The method of treating a charge hydrocarbon stream containing isobutene to prepare a product hydrocarbon stream containing a substantially lesser quantity of isobutene as claimed in claim 1 wherein the mole ratio of isobutene:lower alkanol in said first reaction zone is 1:0.85–0.95.

9. The method of treating a charge hydrocarbon stream containing isobutene to prepare a product hydrocarbon stream containing a substantially lesser quantity of isobutene as claimed in claim 1 wherein the mole ratio of isobutene:lower alkanol in said second reaction zone is 1:4–5.

10. The method of treating a charge hydrocarbon stream containing isobutene to prepare a product hydrocarbon stream containing a substantially lesser quantity of isobutene as claimed in claim 1 wherein said charge hydrocarbon stream contains butadiene.

11. The method of treating a charge hydrocarbon stream containing isobutene to prepare a product hydrocarbon stream containing a substantially lesser quantity of isobutene which comprises contacting said charge hydrocarbon stream containing isobutene and methanol, in mole ratio of isobutene:methanol of 1:0.85–0.95, in a first reaction zone containing acid ion-exchange resin etherification first catalyst, having a hydrogen ion activity of 3.6–3.4 mEqH+/g of resin, thereby forming a first product stream containing methyl tertiary butyl ether plus unreacted hydrocarbons and unreacted isobutene;

separating said first product stream, in a first separation zone, into (i) a bottom containing methyl tertiary butyl ether and (ii) an overhead containing unreacted hydrocarbon and unreacted isobutene;

contacting said overhead containing said charge hydrocarbon stream and unreacted isobutene with excess methanol, in molar amount 4–8 times greater than the molar amount of unreacted isobutene, in a second reaction zone containing acid ion-exchange resin etherification second catalyst, having a hydrogen ion activity of 2.0–2.2 mEqH+/g of resin, thereby forming a second product stream containing the tertiary butyl ether of said lower alkanol plus unreacted hydrocarbons and unreacted methanol;

separating said second product stream, in a second separation zone, into (i) a second overhead stream containing unreacted hydrocarbons and a substantially lesser quantity of isobutene and (ii) a second bottoms stream containing methyl, tertiary butyl ether plus unreacted methanol;

recovering said second overhead stream containing unreacted hydrocarbons and a substantially lesser quantity of isobutene;

recycling said second bottoms stream, containing the tertiary butyl ether of said lower alkanol plus unreacted methanol, to said first reaction zone; and recovering said tertiary butyl ether of said lower alkanol from said bottoms from said first separation zone.

12. The method of treating a charge hydrocarbon stream containing isobutene and also butadiene to prepare a product hydrocarbon stream containing a substantially lesser quantity of isobutene but substantially all of the butadiene which comprises contacting said charge hydrocarbon stream containing isobutene with a deficiency of of lower alkanol in a first reaction zone containing acid ion-exchange resin etherification first catalyst thereby forming a first product stream containing the tertiary butyl ether of said lower alkanol plus hydrocarbon and unreacted isobutene;

separating said first product stream, in a first separation zone, into (i) a bottoms containing the tertiary butyl ether of said lower alkanol and (ii) an overhead containing unreacted hydrocarbons and unreacted isobutene;

contacting said overhead containing said unreacted hydrocarbons and unreacted isobutene with excess lower alkanol, in molar amount greater than the molar amount of unreacted isobutene, in a second reaction zone containing acid ion-exchange resin etherification second catalyst, characterized by a lower hydrogen ion activity than the hydrogen ion activity of said first catalyst, thereby forming a second product stream containing the tertiary butyl ether of said lower alkanol, plus unreacted hydrocarbons and unreacted lower alkanol;

maintaining the space velocity LHSV in the second reaction zone at 0.3–0.7 times that of the first reaction zone;

separating said second product stream, in a second separation zone, into (i) a second overhead stream containing unreacted hydrocarbons and unreacted isobutene and (ii) a second bottoms stream containing the tertiary butyl ether of said lower alkanol, plus unreacted lower alkanol;

recovering said second overhead stream containing unreacted hydrocarbons and unreacted isobutene;

recycling said second bottoms stream, containing the tertiary butyl ether of said lower alkanol plus unreacted methanol, to said first reaction zone; and recovering said tertiary butyl ether of said lower alkanol from said bottoms from said first separation zone.

* * * * *